US006354290B1

(12) United States Patent
Howlett (10) Patent No.: US 6,354,290 B1
(45) Date of Patent: Mar. 12, 2002

(54) INHALATION APPARATUS

(75) Inventor: David Howlett, King's Lynn (GB)

(73) Assignee: Bespak PLC, Norfolk (GB)

( * ) Notice: Subject to any disclaimer, the term of this patent is extended or adjusted under 35 U.S.C. 154(b) by 0 days.

(21) Appl. No.: 09/458,047

(22) Filed: Dec. 10, 1999

(30) Foreign Application Priority Data

Dec. 11, 1998 (GB) .............................................. 9827403

(51) Int. Cl.$^7$ .............................................. A61M 11/60
(52) U.S. Cl. .............................. 128/200.23; 128/200.14
(58) Field of Search ...................... 128/200.14, 200.23, 128/200.24, 200.25, 203.12, 203.15, 203.19–203.25, 200.18, 205.24

(56) References Cited

U.S. PATENT DOCUMENTS

| 3,456,644 | A | * | 7/1969 | Thiel ........................... 128/173 |
| 3,636,949 | A | * | 1/1972 | Kropp .......................... 128/173 |
| 3,789,843 | A | * | 2/1974 | Armstrong et al. .... 128/200.23 |
| 3,814,297 | A | * | 6/1974 | Warren ................... 128/203.12 |
| 3,826,413 | A | * | 7/1974 | Warren ................... 222/402.13 |
| 5,027,806 | A | * | 7/1991 | Zoltan et al. ........... 128/200.23 |
| 5,027,808 | A | * | 7/1991 | Rich et al. .............. 128/203.23 |
| 5,031,610 | A | * | 7/1991 | Armstrong et al. .... 128/200.23 |
| 5,060,643 | A | * | 10/1991 | Rich et al. .............. 128/200.23 |
| 5,119,806 | A | * | 6/1992 | Palson et al. ........... 128/200.14 |
| 5,217,004 | A | * | 6/1993 | Blasnik et al. ......... 128/200.23 |
| 5,224,472 | A | * | 7/1993 | Pesenti et al. ......... 128/200.23 |

FOREIGN PATENT DOCUMENTS

| WO | 1 392 192 | 4/1972 |
| WO | WO 97/37707 | 10/1997 |

* cited by examiner

Primary Examiner—John G. Weiss
Assistant Examiner—Teena Mitchell
(74) Attorney, Agent, or Firm—Smith, Gambrell & Russell LLP (57) ABSTRACT

The present invention relates to an inhalation apparatus for dispensing substances for inhalation and, in particular, but not exclusively, for dispensing medicinal products in aerosol form from a pressurised dispensing container. An inhalation apparatus (1) is provided for dispensing a product comprising housing (20) adapted to receive a pressurised dispensing container (10) and a mouthpiece (22). The apparatus also comprises a duct for conveying, in use, product from the container to the mouthpiece, a sliding seal member (44, 45) movable under action of triggering means (60) between a first position in which the duct is closed and a second position in which the duct is open, wherein a spring means (50) is provided to bias the sliding seal member towards the second position. At least one air inlet (25) is provided for allowing air into the housing and a flow sensor (70) is activatable, by means of an airflow created when a user applies suction to the mouthpiece to activate said triggering means such that said sealing member is moved by said spring means into its second position to allow product to be dispensed into the airflow.

18 Claims, 6 Drawing Sheets

INHALATION APPARATUS

This invention relates to an inhalation apparatus for dispensing substances for inhalation and, in particular, but not exclusively, for dispensing medicinal products in aerosol form from a pressurised dispensing container.

It is well-known when dispensing medicinal products orally, for instance in the treatment of asthma, that the effectiveness of treatment depends to a large extent on the successful delivery of the medicament to the lower part of the lungs of the user. It has been found that the successful delivery of medicament to the lungs of the user is affected by the timing of the delivery in relation to the inhalation cycle of the user. Attempts have been made to coordinate the delivery of medicament with the inhalation cycle of the user and to use the inhalation of the user as the trigger for actuation of the pressurised dispensing container.

However, a disadvantage with a number of these attempts is that the resulting apparatus is difficult to use, requiring skill and training of the user. Thus, these devices are unsuitable for use with small children or the infirm who have difficulty in correctly operating the devices. Another disadvantage has been the inconsistency in performance of the devices. Variations in ambient temperature and pressure tend to alter the material and mechanical properties of components of the devices. This is especially the case for sealing members manufactured from elastomers or rubbers which tend to "stick" when the ambient temperature is raised. This sticking leads to inconsistent movement of the component and to a user of the device having to impart a greater force when inhaling to operate the device.

An object of the present invention is to provide an inhalation apparatus in which mechanical means are used to co-ordinate the delivery of product with the inhalation cycle of the user. It is a further object of the present invention to provide an inhalation apparatus in which the actuation of the apparatus is consistently triggered by the inhalation of the user.

The present invention provides inhalation apparatus for dispensing a product comprising a housing adapted to receive a pressurised dispensing container and a mouthpiece, a duct for conveying, in use, product from the container to the mouthpiece, a sliding seal member movable under action of triggering means between a first position in which the duct is closed and a second position in which the duct is open, wherein a spring means is provided to bias the sliding seal member towards the second position, at least one air inlet for allowing air into the housing and a flow sensor being activatable, by means of an airflow created when a user applies suction to the mouthpiece, to activate said triggering means such that said sealing member is moved by said spring means into its second position to allow product to be dispensed into the airflow.

In a first embodiment, the flow sensor comprises an air inlet valve means biased to seal said at least one air inlet comprising a vane, the vane being movable from a first position, in which the vane seals the at least one air inlet and the sealing member is held in the first position, to a second position in which the vane unseals the at least one air inlet and the sealing member is moved into the second position.

In a second embodiment the flow sensor comprises a diaphragm and a vane, the diaphragm being movable in response to the airflow to contact and move the vane from a first position, in which the sealing member is held in the first position, to a second position in which the sealing member is moved into the second position.

The diaphragm comprises a first rigid element connected to the housing and a second rigid element slidably movable relative thereto, the first and second diaphragm elements being connected by a flexible member.

The triggering means preferably comprise a cantilever being rotatably fixed at one end to the housing and being rotatable from a first position, in which another end of the cantilever is supported by the vane such that the cantilever is in contact with and maintains the sealing member in its first position, to a second position, in which the free end is unsupported by the vane and the cantilever moves out of contact with the sealing member such that the sealing member is able to move to its second position.

Preferably the triggering means further comprises a cam member having a cam surface at least a portion of which is contactable with the cantilever, wherein movement of the cam member moves the cantilever from its second position to its first position.

Alternatively, the triggering means comprises a leaf spring rotatably fixed at one end to the housing and rotatably fixed at the other end to the vane and movable from a first position in which the leaf spring is in contact with and maintains the sealing member in its first position, to a second position, in which the leaf spring moves out of contact with the sealing member such that the sealing member is able to move to its second position.

Preferably the triggering means further comprises a cam member having a cam surface at least a portion of which is contactable with the leaf spring, wherein movement of the cam member moves the leaf spring from its second position to its first position.

As a further alternative, the triggering means comprise a linkage means comprising first and second struts rotatably connected to one another, a distal end of one strut being rotatably fixed to the housing and a distal end of the other strut being rotatably fixed to the vane, the linkage means being movable from a first position in which the linkage means is in contact with and maintains the sealing member in its first position, to a second position, in which the linkage means moves out of contact with the sealing member such that the sealing member is able to move to its second position.

Preferably the triggering means further comprises a cam member having a cam surface at least a portion of which is contactable with the linkage means, wherein movement of the cam member moves the linkage means from its second position to its first position.

Preferably the present invention further comprises a mouthpiece cover moveable from a first position in which the mouthpiece is sealed to a second position in which the mouthpiece is unsealed.

Preferably the cam member is located on the mouthpiece cover, wherein movement of the mouthpiece effects movement of the cam surface relative to the cantilever.

Preferably the present invention further comprises support means for supporting, in use, a pressurised dispensing container and a rod extending between the support and the mouthpiece cover to maintain a fixed distance therebetween when the mouthpiece cover is in its first position, wherein movement of the mouthpiece cover from its first to second position causes the pressurised dispensing container to become unsupported by said rod and allows it to move under bias of a spring to effect depression of a valve stem of the dispensing container.

Preferably the duct means comprises a dispensing channel and a bore extending laterally therefrom and the sealing member is slidable within the dispensing channel, the sealing member comprising a sealing element sealing radially against an inner surface of the dispensing channel, wherein when the sealing member is in its first position, the seal between the sealing element and the dispensing channel is at a position which prevents product from reaching the lateral bore, and when the sealing member is in its second position, the seal is at a position such that product is able to be discharged through the lateral bore into the mouthpiece.

Preferably the sealing element is frusto-conical.

Preferably the sealing element is an elastomer or rubber.

The present invention will now be described, by way of example only, with reference to the accompanying drawings of which.

A first embodiment of an inhalation apparatus according to the present invention is shown in FIGS. 1 to 5. The inhalation apparatus 1 comprises a housing 20 in an upper portion 21 of which is located a generally cylindrical socket 16, for receiving a pressurised dispensing container 10, and in a lower portion 17 of which a mouthpiece 22 is positioned laterally relative to the cylindrical socket 16.

Figure 1:
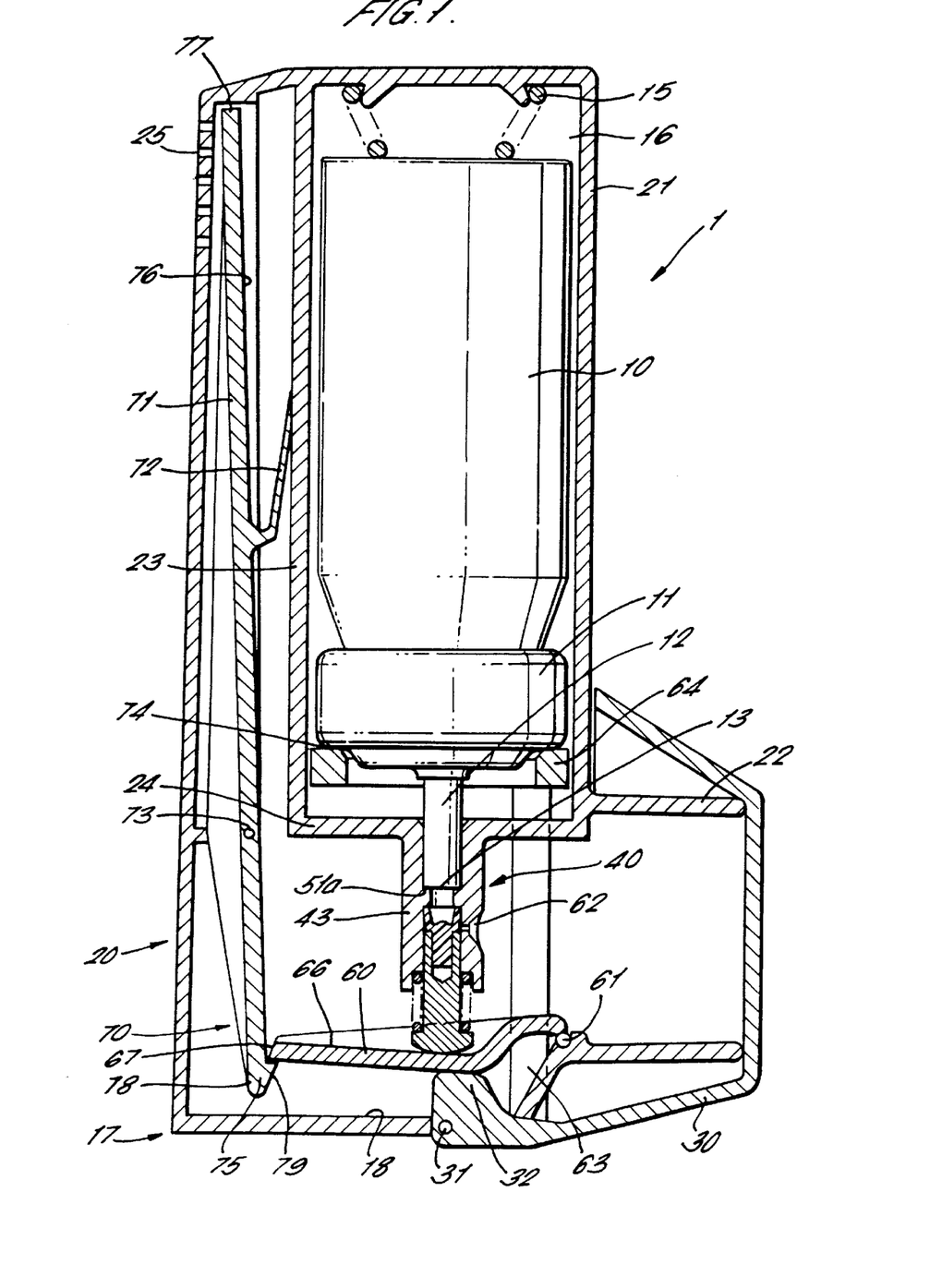
FIG. 1 is a sectional side elevation of a first embodiment of inhalation apparatus according to the present invention.

The socket 16 is defined by a side wall 23 and a bottom wall 24. The side wall 23 may be either planar or arcuate so as to conform closely to the shape of the pressurised dispensing container 10.

Figure 2:
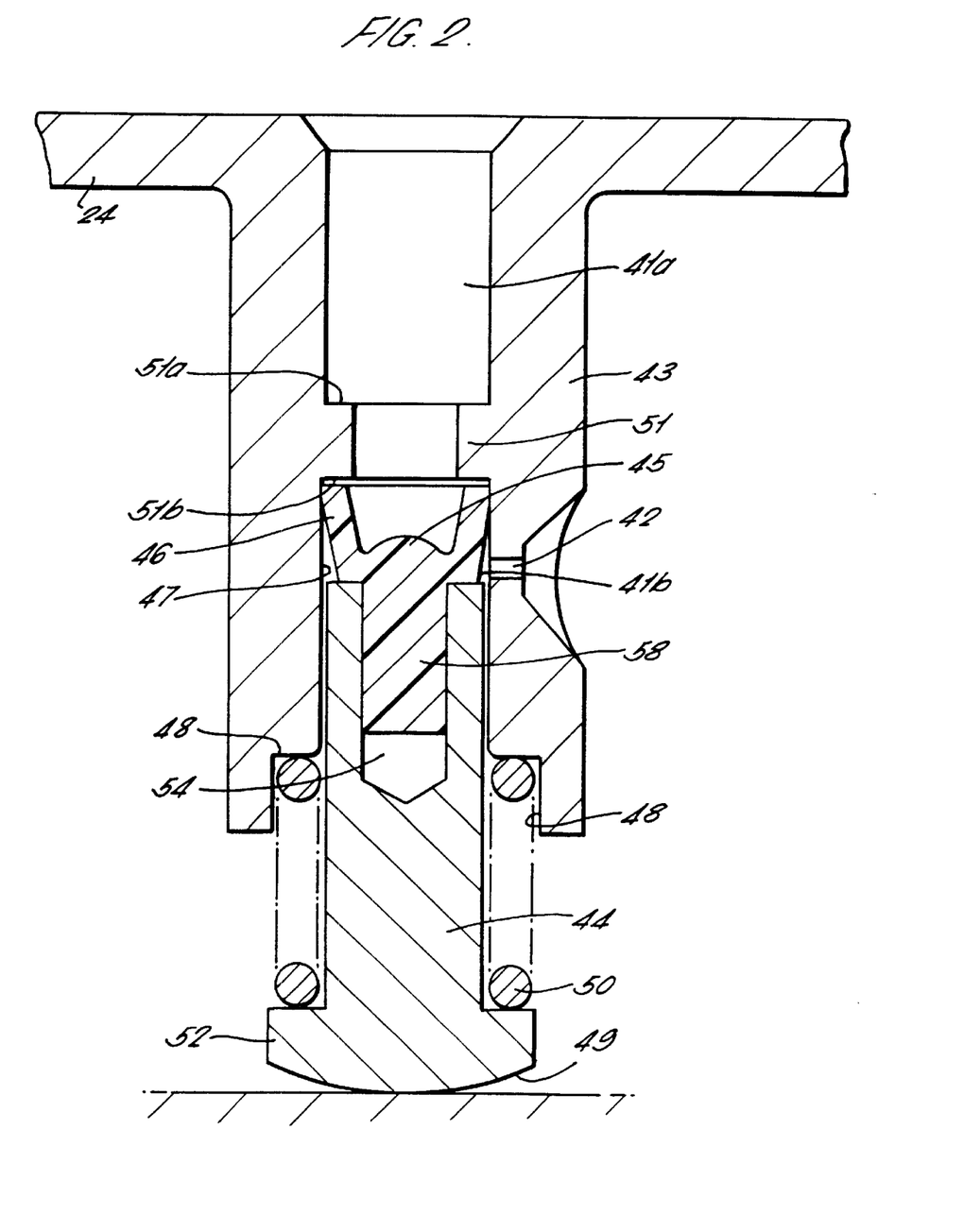
FIG. 2 is a sectional side elevation of a part of the apparatus of FIG. 1 in a first position.

As shown in detail in FIG. 2, a cylindrical extension 43 extends from the socket bottom wall 24 towards the lower end 17 of the housing 20. A bore is formed in the cylindrical extension 43 in an upper end 41a of which bore a valve stem 12 of the dispensing container 10 is received. The bore has a region 51 of narrower diameter separating the upper end 41a and a lower end thereof. An outlet 13 of the valve stem 12 rests against a shoulder 51a formed at the point at which the bore narrows at its upper end 41a. The bore's lower end forms a dispensing channel 41b.

A laterally extending bore 42, directed towards the mouthpiece 22, is provided in a wall of the cylindrical extension 43 communicating with the dispensing channel 41b. The lateral bore 42 terminates with a nozzle 62.

A sealing member 44, 45 is inserted in the dispensing channel 41b and is axially slidable therein. The sealing member comprises a body portion 44 and a sealing plug 45. The sealing plug 45 is preferably formed from an elastomeric or rubber material with good sealing properties. The body portion 44 is preferably formed from polyester, nylon or other suitable material. The body portion 55 has a radially extending annular flange 52 at one end and an axial bore 54 which extends from the other end part-way along the length of the body portion 55. The sealing plug 45 has a spigot 58, which is fixedly received in the axial bore 54 of the body portion 44, and a frusto-conical extension 46 which extends divergently from the spigot 58. The sides of plug 45 seal against an inner cylindrical surface 47 of the dispensing channel 41b. The sealing member 44 is biased by means of a first spring 50 disposed between the flange 52 and a recessed step formation 48 formed at a lower end 59 of the cylindrical extension 43.

The external diameter of the divergent end of the frusto-conical extension 46 is greater than the internal diameter of the dispensing channel 41b. Consequently the frusto-conical portion 46 is inwardly compressed upon insertion into the dispensing channel 41b leading to a resultant outward radial force being exerted by the frusto-conical portion 46 on the inner surface 47 of the dispensing channel 40. This results in an improvement in the integrity of the seal between the frusto-conical extension 46 and the inner surface 47 compared to a seal in which two parallel surfaces are in contact. The integrity of the seal is also less prone to "sticking" when the ambient temperature is raised or suffering from degradation over time. Thus the sealing plug 45 forms an effective seal within the dispensing channel 40.

The flange 52 of the sealing member body portion 44 has an arcuate surface which, before actuation of the apparatus 1, rests against an upper surface 66 of a cantilever 60. The cantilever 60 is mounted in the housing 20 at one end via a pivot 61 located approximately at the junction between the mouthpiece 22 and the cylindrical portion 21. The other end 67 of the cantilever 60 is free so that the cantilever may rotate about the pivot 61.

A cover 30 is provided, for hygiene reasons, to cover the mouthpiece 22 when the apparatus 1 is not in use. The mouthpiece cover 30 is attached to the housing 20 by a hinge 31 located beneath the cylindrical extension 43. The mouthpiece cover 30 has a cam member defining a cam surface 32 which contacts and supports the cantilever 60 when the mouthpiece cover 30 is closed, (i.e. in a non-operational condition of the inhalation apparatus), as shown in FIG. 1. When the mouthpiece cover 30 is in the closed position, the cam surface 32 causes the cantilever 60 to adopt a first raised position. In this position, the sealing member 44, 45 which is resting on the top of the cantilever 60, is held, as shown in FIG. 2, with the frusto-conical extension 46 of the sealing plug 45 pressed against the shoulders 51b between the dispensing channel 41b and the restricted portion 51 of the bore. The first spring 50 is compressed in this condition.

A second spring 15 is disposed between an upper wall of the housing 20 and the base of the pressurised dispensing container 10. The second spring 15 biases the pressurised dispensing container 10, as shown in FIG. 1, into a position corresponding to actuation of the pressurised dispensing container 10. A ferrule 11 (or equivalent component) of the pressurised dispensing container 10 rests against a generally annular bearing ring 64 provided in a lower end of the container socket 16. A rod 63 extends between the annular bearing ring 64 and the mouthpiece cover 30. With the mouthpiece cover 30 in the closed position, the lower end of the rod 63 abuts against the mouthpiece cover 30 causing the bearing ring 64 to be supported in a raised position. The length of the rod 63 is such that, with the mouthpiece cover 30 in the closed position, the bearing ring 64 is supported at a finite distance above the receiving portion base wall 24 and the pressurised dispensing container 10 is held in a raised position pushing against the bias of the second spring 15.

One or more air inlets 25 are provided at an upper end of the housing 20 in a wall which does not form part of the container socket 16. A vane 70 is disposed within the housing 20 extending along substantially the entire axial length of the housing 20. The vane 70 is attached to the housing 20 by means of a pin 73, which is preferably located toward a lower end of the vane 70, about which the vane 70 is pivotable. A flexible flange 72 extends from one side 76 of the vane means 70 thereof to contact the side wall 23 of the container socket 16. The flexible flange 72 biases an upper end 77 of the vane 70 away from the container socket 16 to sealingly cover the air inlets 25. Thus the air inlets 25 and vane 70 together form an air inlet valve means which controls the flow of air through the housing 20 when a user applies suction to the mouthpiece 22. A hook 75 is formed at a lower end 78 of the vane 20. When the mouthpiece cover 30 is in a closed position, the free end 67 of the cantilever 60 rests on the hook 75, as shown in FIG. 1.

In use, a user of the inhalation apparatus 1 starts to open the mouthpiece cover 30, pivoting the cover 30 about the cover hinge 31. As the mouthpiece cover 30 is thus rotated, the rod 63 becomes unsupported by the mouthpiece cover 30 and the rod 63, bearing ring 64 and pressurised dispensing container 10 move under the biasing force of the secondary spring means 15 towards the base 24 of the container socket 16. Since the valve stem 12 already abuts against the shoulder 51a in the cylindrical extension 43, this movement of the container 10 causes the valve stem 12 to be depressed relative thereto, thereby dispensing a dose of product through the valve stem outlet 13 into the bore in the cylindrical extension 43. The product, which at this stage is still highly pressurised, is contained within the dispensing channel 40 and is prevented from passing into the mouthpiece 22 since the seal between the frustoconical extension 46 of the sealing plug 45 and the inner surface 47 of the dispensing channel 40 is between the restricted portion 51 and the orifice 42 (as shown in FIG. 2).

As the mouthpiece cover 30 is further rotated, the cam surface 32 moves out of contact with the cantilever 60. However, at this stage, the cantilever 60 does not move since the free end 67 of the cantilever 60 is supported by the hook 75.

The user of the apparatus 1 then inhales through the mouthpiece 22. Initially, no air can enter the housing 70 as the vane 70 seals the air inlets 25. However, as the user continues to inhale, a pressure differential is set up across the vane 70 which causes it to pivot about the pin 73. The positioning of the hinge 73 towards the lower end 78 of the vane 70 reduces the inhalation effort required by the user to rotate the vane 70. As the vane 70 rotates, the flexible flange 72 is compressed against the side wall 23. The movement of the vane 70 unseals the air inlets 25 and air is able to flow through the housing 20, out of the mouthpiece 22 and into the user's lungs.

Figure 3:
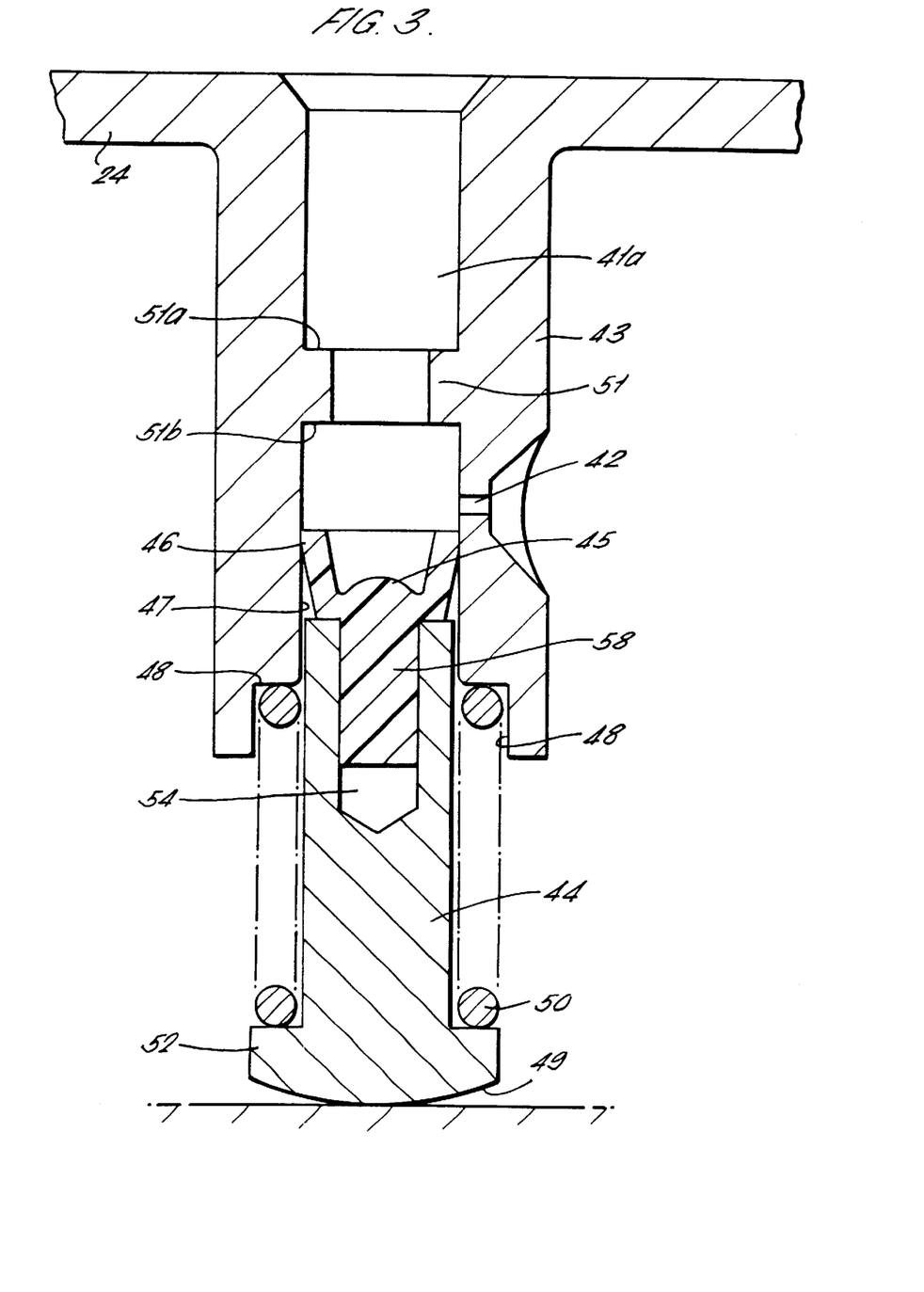
FIG. 3 is a sectional side elevation of the part of the apparatus of FIG. 1 in a second position.
Figure 4:
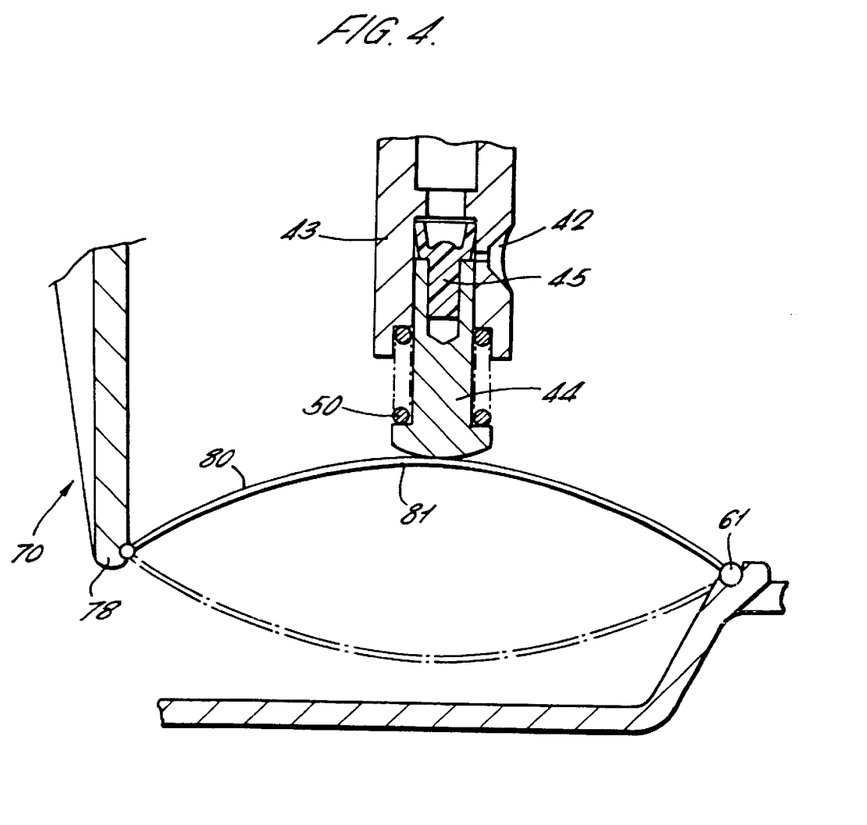
FIG. 4 is a sectional side elevation of part of an alternative inhalation apparatus according to the present invention with some items removed for clarity.
Figure 5:
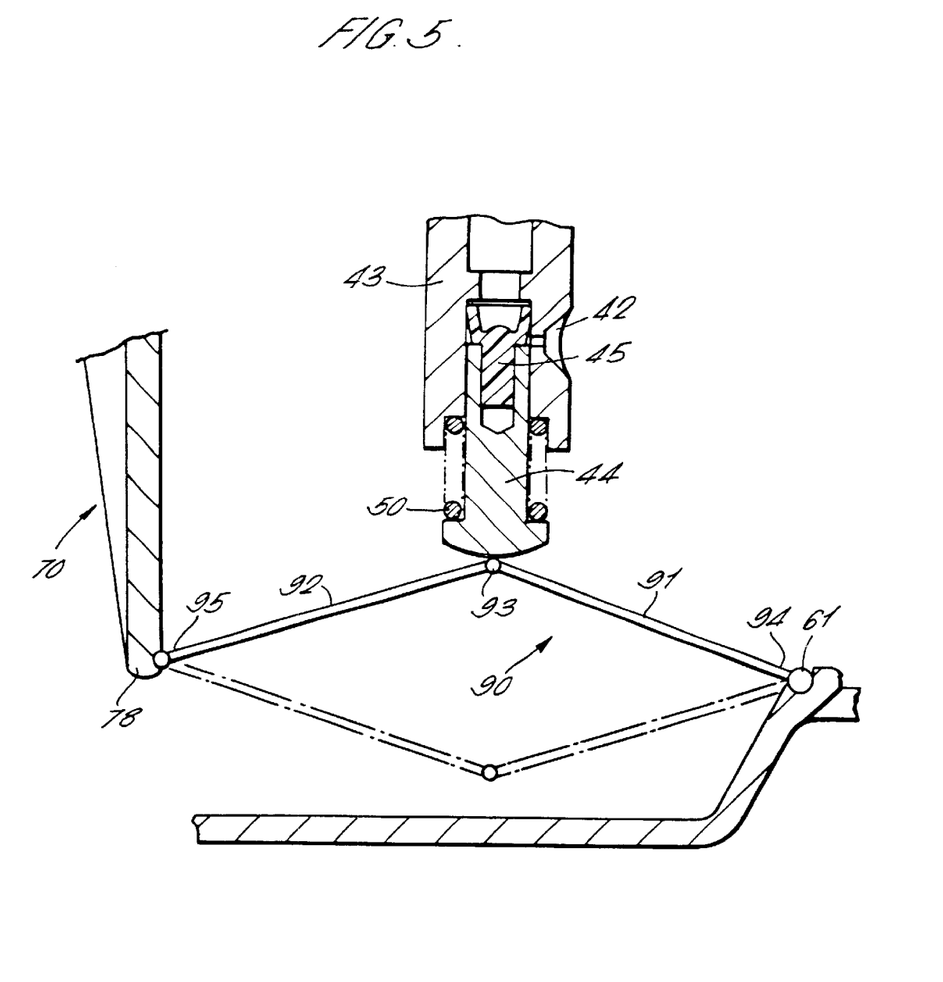
FIG. 5 is a sectional side elevation of part of a further alternative inhalation apparatus according to the present invention with some parts removed for clarity.

As the vane 70 rotates further about the hinge 73, the hook 75 moves away from the free end 67 of the cantilever 60, which drops downwardly under gravity and the biasing force of the first spring 50 so that it rests on the bottom 18 of the housing 20. As the cantilever 60 drops, the sealing member 44 moves under action of the first spring 50 within the bore of the cylindrical extension 43, into the position as shown in FIG. 3. Thus the cantilever 60 together with the hook 75 of the vane 70 form a triggering means which controls the movement of the sealing member 44. As the sealing member 44 moves, the point of sealing contact between the frusto-conical portion 46 and the inner surface 47 of the dispensing channel 40 moves past the level of the orifice 42 thereby opening communication between the channel 40 and orifice 42. At this point, the still highly pressurised product contained within the dispensing channel 40 is discharged through the orifice 42 as an aerosol and is entrained in the airflow through the housing 20 and is inhaled into the user's lungs. Variation of the dimensions of one or more of the vane 70, hook 75, cantilever 60 and sealing member 44 can be used to adjust the timing of the dispensing of the product to co-ordinate delivery with the user's inhalation cycle.

When the user of the apparatus 1 stops inhaling, the vane 70 returns under the biasing force of the flexible extension 72 to seal the air inlets 25. At this point, the cantilever 60 is still in its lowered position with its free end 67 resting against the bottom 18 of the housing 20.

As the user of the apparatus 1 closes the mouthpiece cover 30 the cam surface 32 comes back into contact with the cantilever 60 causing the cantilever 60 to rotate about the hinge 61. As the cantilever 60 rotates, it pushes the sealing member 44 against the bias of the spring 50 axially relative to the cylindrical extension 43 back into its original position sealing the orifice 42 from the dispensing channel 40. Also, as the cantilever 60 rotates, the free end 67 of the cantilever 60 passes the formation 75 on the vane 70. The movement of the free end 67 of the cantilever 60 is accommodated by a ramp 79 on a lower surface of the hook 75. Thus, the movement of the free end 67 of the cantilever 60 causes the vane 70 to rotate slightly until the free end 67 of the cantilever 60 has passed the hook 75, at which point the vane 70 returns to its original position under the biasing force of the flexible flange 72. In this way, closing the mouthpiece cover 30 resets the sealing means, air inlet valve means and triggering means of the apparatus 1 to their first positions such that the apparatus is ready for further actuations.

FIG. 4 shows a further embodiment of the present invention. In this embodiment the cantilever 60 is replaced by a leaf spring 80 which is rotatably connected at one end to the hinge 61 and at the other end to the lower end 78 of the vane 70. The leaf spring 80 has two stable positions. In a first position the leaf spring 80 arcs upwardly towards the sealing member such that a central portion 81 of the leaf spring contacts and biases the body portion 44 upwardly into its raised position in which the sealing means is closed. In a second position the leaf spring 80 arcs downwardly away from the sealing member such that the central portion 81 of the leaf spring is out of contact with the body portion 44.

The apparatus operates in a similar manner to the first described embodiment. In a non-operative position of the apparatus the leaf spring 80 is in its first stable position and the sealing means is closed. Inhalation by the user, as with the first described embodiment, results in movement of the base 78 of the vane 70. This movement forces the leaf spring 80 to "snap-through" into its second stable position in which the body portion and sealing plug 45 are free to move downwardly under the bias of spring 50 to open the sealing means and discharge the pressurised product through the orifice 42. The triggering means of the leaf spring 80 is reset in a similar manner to the first described embodiment. As the mouthpiece cover 30 is closed the cam surface 32 (not shown in FIG. 4 for clarity) contacts the leaf spring 80 and biases it upwardly resulting in the leaf spring "snapping-through" to its first stable position in which the apparatus is ready for further actuations.

FIG. 5 shows a third embodiment of the present invention. In this embodiment the cantilever 60 is replaced by an over-centre linkage means 90 which comprises two rigid struts 91 and 92 rotatably connected to one another at a centre hinge 93. The distal end 94 of the first strut 91 is rotatably connected to hinge 61 and the distal end 95 of the second strut 92 is rotatably connected to the base 78 of vane 70. The linkage means 90 has two stable positions. In a first position the linkage means 90 points upwardly towards the sealing member such that the central hinge 93 of the linkage means 90 contacts and biases the body portion 44 upwardly into its raised position in which the sealing means is closed. In a second position the linkage means 90 points downwardly away from the sealing member such that the central hinge 93 of the linkage means 90 is out of contact with the body portion 44.

The apparatus operates in a similar manner to the first described embodiment. In a non-operative position of the apparatus the linkage means 90 is in its first stable position and the sealing means is closed. Inhalation by the user, as with the first described embodiment, results in movement of the base 78 of the vane 70. This movement forces the linkage means 90 to "snap-through" into its second stable position in which the body portion and sealing plug 45 are free to move downwardly under the bias of spring 50 to open the sealing means and discharge the pressurised product through the orifice 42. The triggering means of the linkage means 90 is reset in a similar manner to the first described embodiment. As the mouthpiece cover 30 is closed the cam surface 32 (not shown in FIG. 5 for clarity) contacts the linkage means 90 and biases it upwardly resulting in the linkage means 90 "snapping-through" to its first stable position in which the apparatus is ready for further actuations.

Figure 6:
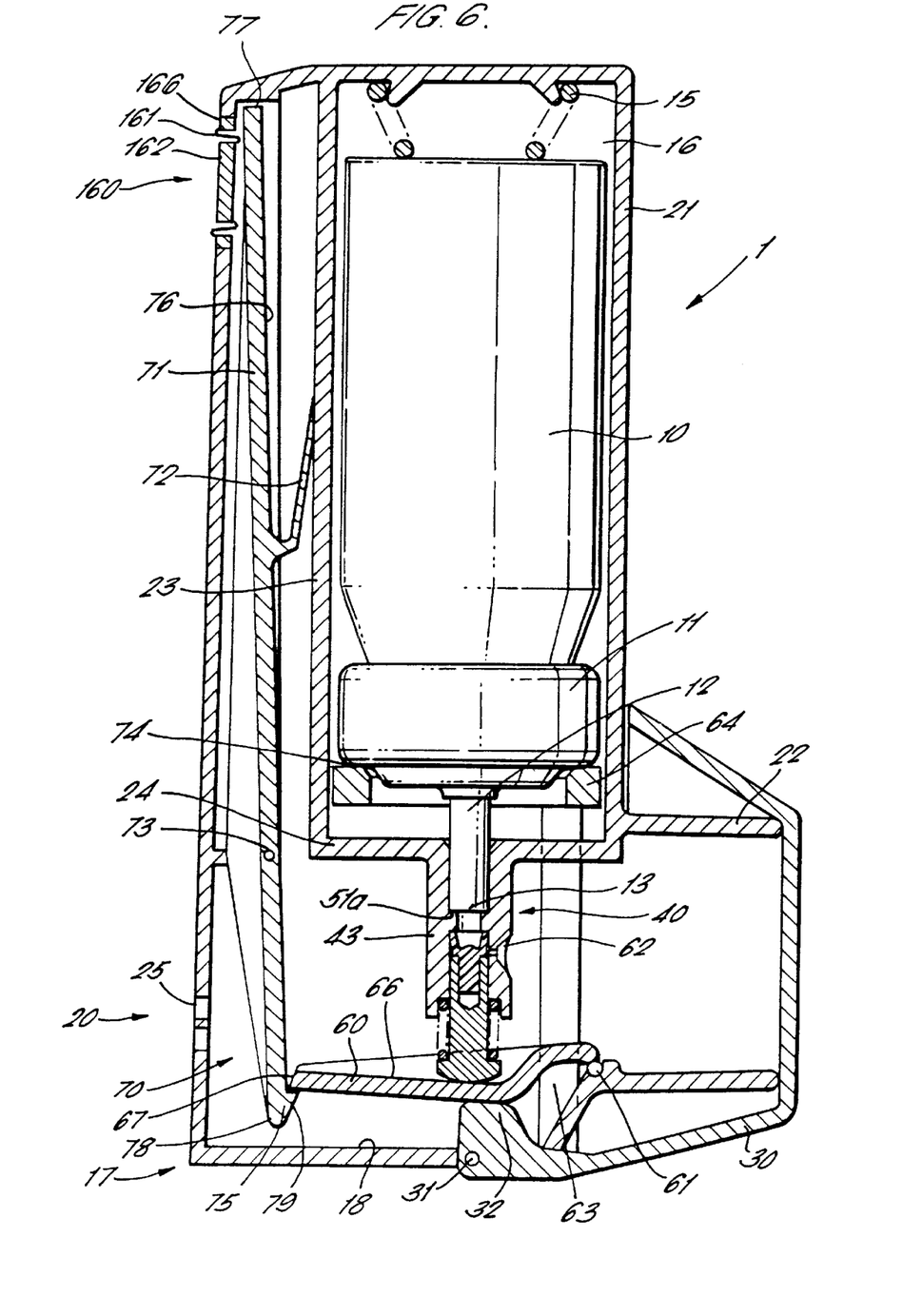
FIG. 6 is a sectional side elevation of a second embodiment of inhalation apparatus according to the present invention.

FIG. 6 shows a further embodiment of apparatus according to the present invention. This embodiment is identical to the first embodiment except with regard to the air inlets 25.

Instead of the one or more air inlets 25 being disposed at an upper end of the housing 20, the one or more air inlets are disposed towards a lower end of the housing. At an upper end of the housing 20, aligned with the upper end of the vane 70, is provided an opening closed by a diaphragm 160. The diaphragm 160 comprises two essentially rigid elements. A first is a ring-shaped element 166 which is attached to the housing 20 around the opening. The second is an annular element 162 which extends across the opening. The first and second elements 166, 162 of the diaphragm 160 are connected by a flexible member 161, preferably in the form of a rolling seal which allows displacement of the second diaphragm element 162 relative to the first diaphragm element 166 from a first position in which the second diaphragm element 162 is out of contact with the vane 70 to a second position in which the second diaphragm element 162 contacts and moves the upper end of vane 70.

In use, a user inhales through mouthpiece portion 22 creating a flow of air from the one or more air inlets 25 through the apparatus 1. The airflow creates a relative pressure drop in the apparatus 1 compared to the exterior. As a result the second diaphragm element 162 is moved to its second position in which it contacts and rotates the upper end of vane 70. The remainder of the operation of the second embodiment is the same as the first embodiment.

It should be noted that any of the first, second, or third embodiments described above may be incorporated with the diaphragm 160 of the latter embodiment.

In addition the apparatus according to the present invention may incorporate a dosage counter unit for recording either the number of dosages of product remaining within the dispensing container or the number of dosages dispensed.

What is claimed is:

1. Inhalation apparatus for dispensing a product comprising a housing adapted to receive a pressurised dispensing container and a mouthpiece, a duct for conveying, in use, product from the container to the mouthpiece, a sliding seal member movable under action of triggering means between a first position in which the duct is closed and a second position in which the duct is open, wherein a spring means is provided to bias the sliding seal member towards the second position, at least one air inlet for allowing air into the housing and a flow sensor being activatable, by means of an airflow created when a user applies suction to the mouthpiece, to activate said triggering means such that said sealing member is moved by said spring means into its second position to allow product to be dispensed into the airflow.

2. Inhalation apparatus as claimed in claim 1, wherein the flow sensor comprises an air inlet valve means biased to seal said at least one air inlet comprising a vane, the vane being movable from a first position, in which the vane seals the at least one air inlet and the sealing member is held in the first position, to a second position in which the vane unseals the at least one air inlet and the sealing member is moved into the second position.

3. Inhalation apparatus as claimed in claim 2, wherein the triggering means comprise a cantilever being rotatably fixed at one end to the housing and being rotatable from a first position, in which a free end of the cantilever is supported by the vane such that the cantilever is in contact with and maintains the sealing member in its first position, to a second position, in which the free end is unsupported by the vane and the cantilever moves out of contact with the sealing member such that the sealing member is able to move to its second position.

4. Inhalation apparatus as claimed in claim 3, wherein the triggering means further comprises a cam member having a cam surface at least a portion of which is contactable with the cantilever, wherein movement of the cam member moves the cantilever from its second position to its first position.

5. Inhalation apparatus as claimed in claim 2, wherein the triggering means comprise a leaf spring rotatably connected at one end to the housing and rotatably connected at the other end to the vane and movable from a first position in which the leaf spring is in contact with and maintains the sealing member in its first position, to a second position, in which the leaf spring moves out of contact with the sealing member such that the sealing member is able to move to its second position.

6. Inhalation apparatus as claimed in claim 5, wherein the triggering means further comprises a cam member having a cam surface at least a portion of which is contactable with the leaf spring, wherein movement of the cam member moves the leaf spring from its second position to its first position.

7. Inhalation apparatus as claimed in claim 2, wherein the triggering means comprise a linkage means comprising first and second struts rotatably connected to one another, a distal end of one strut being rotatably fixed to the housing and a distal end of the other strut being rotatably fixed to the vane, the linkage means being movable from a first position in which the linkage means is in contact with and maintains the sealing member in its first position, to a second position, in which the linkage means moves out of contact with the sealing member such that the sealing member is able to move to its second position.

8. Inhalation apparatus as claimed in claim 7, wherein the triggering means further comprises a cam member having a cam surface at least a portion of which is contactable with the linkage means, wherein movement of the cam member moves the linkage means from its second position to its first position.

9. Inhalation apparatus as claimed in claim 1, wherein the flow sensor comprises a diaphragm and a vane, the diaphragm being movable in response to the airflow to contact and move the vane from a first position, in which the sealing member is held in the first position, to a second position in which the sealing member is moved into the second position.

10. Inhalation apparatus as claimed in claim 9, wherein the diaphragm comprises a first rigid element connected to the housing and a second rigid element slidably movable relative thereto, the first and second diaphragm elements being connected by a flexible member.

11. Inhalation apparatus as claimed in claim 1, further comprising a mouthpiece cover moveable from a first position in which the mouthpiece is sealed to a second position in which the mouthpiece is unsealed.

12. Inhalation apparatus as claimed in claim 11 wherein said triggering means includes a cam member and said cam member being located on the mouthpiece cover, wherein movement of the mouthpiece effects movement of the cam.

13. Inhalation apparatus as claimed in claim 12 wherein said triggering means includes a cantilever rotably fixed at one end to the housing and said cam having a can surface at least a portion of which is contactable with the cantilever, and wherein movements of the mouthpiece effects movement of the cam surface relative to the cantilever.

14. Inhalation apparatus as claimed in claim 11, further comprising support means for supporting, in use, a pressurised dispensing container having a valve stem and a rod extending between the support and the mouthpiece cover to maintain a fixed distance therebetween when the mouthpiece cover is in its first position, wherein movement of the mouthpiece cover from its first to second position causes the pressurized dispensing container to become unsupported by said rod and allows it to move under bias of a spring to effect depression of the valve stem of the dispensing container.

15. Inhalation apparatus as claimed in claim 1 in which the duct means comprises a dispensing channel having an inner surface and a bore extending between said dispensing channel and the mouthpiece and the sealing member is slidable within the dispensing channel, the sealing member comprising a sealing element sealing against the inner surface of the dispensing channel, wherein when the sealing member is in its first position, the seal between the sealing element and the dispensing channel is at a position which prevents product from reaching the bore, and when the sealing member is in its second position, the seal is at a position such that product is able to be discharged through the bore into the mouthpiece.

16. Inhalation apparatus as claimed in claim 15, wherein the sealing element is frusto-conical.

17. Inhalation apparatus as claimed in claim 15, wherein the sealing element is an elastomer or rubber.

18. Inhalation apparatus as claimed in claim 1, in combination with a pressurised dispensing container comprising a metering valve, propellant and product to be dispensed.

* * * * *